United States Patent [19]

Vale, Jr. et al.

[11] 4,415,558
[45] Nov. 15, 1983

[54] CRF AND ANALOGS

[75] Inventors: Wylie W. Vale, Jr., La Jolla; Joachim Spiess, Encinatas; Catherine L. Rivier; Jean E. F. Rivier, both of La Jolla, all of Calif.

[73] Assignee: The Salk Institute for Biological Studies, San Diego, Calif.

[21] Appl. No.: 378,999

[22] Filed: May 17, 1982

Related U.S. Application Data

[63] Continuation-in-part of Ser. No. 271,624, Jun. 8, 1981, abandoned.

[51] Int. Cl.$^3$ ..................... A61K 37/00; C07C 103/52
[52] U.S. Cl. ............................... 424/177; 260/112.5 R
[58] Field of Search ................... 260/112.5 R; 424/177

[56] References Cited

PUBLICATIONS

J. Spiess, et al., Proc. Nat'L Acad. Sci. 78, No. 10, pp. 6517–6521 (1981).
W. Vale, et al., Endocrinology 103, 1910–1915 1978.
Computer Printout.
"Substances Modulating the Secretion of ACTH by Cultured-Anterior Pituitary Cells", Fed. Proc. 36 (1977).
The Role of Peptides in Neuronal Function, edited by Barker, et al., 1980 "Regulation of Hypophyseal Corticotropic Cells", Vale et al., pp. 432–454.
Active Polypeptides: from Amphibian Skin to Gastrointestinal Tract and Brain of Mammals, Erspamer, et al., Trends in Pharm. Sci. 10/80 pp. 391–395.

*Primary Examiner*—Delbert R. Phillips
*Attorney, Agent, or Firm*—Fitch, Even, Tabin & Flannery

[57] ABSTRACT

CRF (Corticotropin Releasing Factor) has the formula: H-Ser-Gln-Glu-Pro-Pro-Ile-Ser-Leu-Asp-Leu-Thr-Phe-His-Leu-Leu-Arg-Glu-Val-Leu-Glu-Met-Thr-Lys-Ala-Asp-Gln-Leu-Ala-Gln-Gln-Ala-His-Ser-Asn-Arg-Lys-Leu-Leu-Asp-Ile-Ala-NH$_2$.

Analogs have been synthesized that are at least as potent as CRF, and CRF or these analogs or pharmaceutically acceptable salts thereof, dispersed in a pharmaceutically acceptable liquid or solid carrier, can be administered to mammals to achieve a substantial elevation of ACTH, β-endorphin, β-lipotropin and corticosterone levels and/or a lowering of blood pressure over an extended period of time. In the analogs, one or more of the first three N-terminal residues may be deleted or may be substituted by a peptide up to 10 amino acids long and/or by an acylating agent containing up to 7 carbon atoms. Ala in the 41-position may also be substituted or deleted so long as the remaining C-terminus is amidated. Several other substitutions may also be made throughout the chain.

31 Claims, No Drawings

CRF AND ANALOGS

The invention was made in the course of work under a grant or award from the Department of Health and Human services.

This application is a continuation-in-part of our Ser. No. 271,624, filed June 8, 1981 and now abandoned.

This invention is directed to peptides related to the hentetracontapeptide CRF and to methods for pharmaceutical treatment of mammals using such peptides. More specifically, the invention relates to CRF and analogs of CRF, to pharmaceutical compositions containing CRF or such analogs and to methods of treatment of mammals using CRF or such analogs.

BACKGROUND OF THE INVENTION

Experimental and clinical observations have supported the concept that the hypothalamus plays a key role in the regulation of adenohypophysial corticotropic cells secretory functions. Over 25 years ago, Guillemin, Rosenberg and Saffran and Schally independently demonstrated the presence of factors in hypothalamus which would increase the rate of ACTH secretion by the pituitary gland incubated in vitro or maintained in an organ culture. None of the secretagogs characterized to date meets the criteria expected of a physiologic corticotropin releasing factor, CRF. Accordingly the purification of a large CRF has been pursued. Starting material for the purification was an early side fraction of the 490,000 ovine hypothalamic fragments originally extracted in the Laboratory for Neuroendocrinology at The Salk Institute, as described in Burgus et al. *Hypothalamus and Endocrine Functions* (F. Labrie et al. eds.) Plenum, New York, 1976, p. 355. None of the earlier attempts at purification were felt to have obtained this large molecular weight CRF in a purity of greater than about 1%.

Sauvagine is a 40-residue, amidated generally similar peptide which was isolated from the skin of the South American frog Phyllomedusa sauvagei, was characterized by Erspamer et al. and was described in *Regulatory Peptides*, Vol. 2 (1981), pp. 1–13. Sauvagine has the formula:
pGlu-Gly-Pro-Pro-Ile-Ser-Ile-Asp-Leu-Ser-Leu-Glu-
  Leu-Leu-Arg-Lys-Met-Ile-Glu-Ile-Glu-Lys-Gln-
  Glu-Lys-Glu-Lys-Gln-Gln-Ala-Ala-Asn-Asn-Arg-
  Leu-Leu-Leu-Asp-Thr-Ile-$NH_2$.
Sauvagine has been reported to have biological activity in lowering blood pressure in mammals and in stimulating the secretion of ACTH and $\beta$-endorphin.

SUMMARY OF THE INVENTION

CRF has now been isolated, purified and characterized as a hentetracontapeptide having the formula:
H-Ser-Gln-Glu-Pro-Pro-Ile-Ser-Leu-Asp-Leu-Thr-
  Phe-His-Leu-Leu-Arg-Glu-Val-Leu-Glu-Met-Thr-
  Lys-Ala-Asp-Gln-Leu-Ala-Gln-Gln-Ala-His-Ser-
  Asn-Arg-Lys-Leu-Leu-Asp-Ile-Ala-$NH_2$.
It may alternatively be referred to as Amunine. The synthesis of the 41-residue peptide has been completed, and both the isolated CRF and the synthetic CRF have been found to stimulate ACTH and $\beta$-endorphin activies in vitro and in vivo. Synthetic CRF has been found to substantially lower blood pressure for an extended time period. As a result CRF has been made available in substantially pure form (i.e. substantially free of the remainder of a crude biological extract or of related synthetic replicates), and a purity of at least about 93% or higher is practically obtainable and useful for clinical testing.

Analogs of the 41-residue peptide CRF having the following formula have at least substantially the same biological activity:
Z-$R_1$-Pro-Pro-Ile-Ser-$R_8$-Asp-Leu-$R_{11}$-$R_{12}$-
  $R_{13}$-Leu-Leu-Arg-$R_{17}$-$R_{18}$-$R_{19}$-Glu-$R_{21}$-
  $R_{22}$-Lys-$R_{24}$-$R_{25}$-$R_{26}$-$R_{27}$-$R_{28}$-Gln-Gln-Ala-$R_{32}$-$R_{33}$-
  Asn-Arg-$R_{36}$-Leu-Leu-Asp-$R_{40}$-$R_{41}$-$NH_2$
wherein Z is hydrogen or an acyl group having 7 or less carbon atoms and/or a peptide up to 10 residues long; $R_1$ is Ser-Gln-Glu or pGlu-Gly or Gln-Glu or Glu or D-Ser-Gln-Glu or D-pGlu-Gly or des$R_1$; $R_8$, $R_{12}$, $R_{19}$, $R_{24}$ and $R_{40}$ are selected from the group consisting of Leu, Ile, Ala, Gly, Val, Nle, Phe and Gln; $R_{11}$ is Thr or Ser; $R_{13}$ is His, Tyr or Glu; $R_{17}$ is Glu or Lys; $R_{18}$ is Val or Met; $R_{21}$ is Met, Met(O), Ile, Ala, Leu, Gly, Nle, Val, Phe or Gln; $R_{22}$ is Thr or Glu; $R_{25}$ is Asp or Glu; $R_{26}$ is Gln or Lys; $R_{27}$ is Leu, Ile, Ala, Gly, Val, Nle, Phe, Asp, Asn, Gln or Glu; $R_{28}$ is Ala or Lys; $R_{32}$ is His, Tyr or Ala; $R_{33}$ is Ser, Asn, Thr or Ala; $R_{36}$ is Lys or Leu; $R_{41}$ is Ala, Ile, Gly, Val, Leu, Nle, Phe, Gln or des $R_{41}$, provided however that when $R_{13}$ is His, then $R_{17}$ is Glu, $R_{18}$ is Val, $R_{22}$ is Thr, $R_{26}$ is Gln, $R_{28}$ is Ala, and $R_{36}$ is Lys; and provided that when $R_{13}$ is Glu, $R_{17}$ is Lys, $R_{18}$ is Met, $R_{22}$ is Glu, $R_{26}$ is Lys, $R_{28}$ is Lys, $R_{32}$ is Ala and $R_{36}$ is Leu, then either $R_1$ is not pGlu-Gly or $R_8$ is not Ile or $R_{11}$ is Thr or $R_{12}$ is not Leu or $R_{19}$ is not Ile or $R_{21}$ is not Ile or $R_{24}$ is not Gln or $R_{27}$ is not glu or $R_{33}$ is not Asn or $R_{40}$ is not Thr or $R_{41}$ is not Ile.

Pharmaceutical compositions in accordance with the invention include CRF or its analogs, or nontoxic addition salts thereof, dispersed in a pharmaceutically acceptable liquid or solid carrier. The administration of such peptides or pharmaceutically acceptable addition salts thereof to mammals in accordance with the invention may be carried out for the regulation of secretion of ACTH, $\beta$-endorphin, $\beta$-lipotropin, and corticosterone and/or for the lowering of blood pressure and/or affecting mood, behavioral and gastrointestinal functions.

DETAILED DESCRIPTION OF THE PREFERRED EMBODIMENTS

CRF has been isolated from ovine hypothalamic extracts, purified and characterized. The nomenclature used to define the peptides is that specified by Schroder & Lubke, "The Peptides", Academic Press (1965) wherein, in accordance with conventional representation, the amino group appears to the left and the carboxyl group to the right. Where the amino acid residue has isomeric forms, it is the L-form of the amino acid that is represented unless otherwise expressly indicated.

The invention provides CRF and analogs of CRF having the following formula:
Z-$R_1$-Pro-Pro-Ile-Ser-$R_8$-Asp-Leu-$R_{11}$-$R_{12}$-
  $R_{13}$-Leu-Leu-Arg-$R_{17}$-$R_{18}$-$R_{19}$-Glu-$R_{21}$-
  $R_{22}$-Lys-$R_{24}$-$R_{25}$-$R_{26}$-$R_{27}$-$R_{28}$-Gln-Gln-Ala-$R_{32}$-$R_{33}$-
  Asn-Arg-$R_{36}$-Leu-Leu-Asp-$R_{40}$-$R_{41}$-$NH_2$
wherein Z is hydrogen or an acyl group having 7 or less carbon atoms and/or a peptide up to 10 residues long; $R_1$ is Ser-Gln-Glu or pGlu-Gly or Gln-Glu or Glu or D-Ser-Gln-Glu or D-pGlu-Gly or des$R_1$; $R_8$, $R_{12}$, $R_{19}$, $R_{24}$ and $R_{40}$ are selected from the group consisting of Leu, Ile, Ala, Gly, Val, Nle, Phe and Gln; $R_{11}$ is Thr or Ser; $R_{13}$ is His, Tyr or Glu; $R_{17}$ is Glu or Lys; $R_{18}$ is Val or Met; $R_{21}$ is Met, Met(O), Ile, Ala, Leu, Gly, Nle, Val, Phe or Gln; $R_{22}$ is Thr or Glu; $R_{25}$ is Asp or Glu; $R_{26}$ is Gln or Lys; $R_{27}$ is Leu, Ile, Ala, Gly, Val, Nle, Phe, Asp, Asn, Gln or Glu; $R_{28}$ is Ala or Lys; $R_{32}$ is His, Tyr or Ala; $R_{33}$ is Ser, Asn, Thr or Ala; $R_{36}$ is Lys or Leu; $R_{41}$ is Ala, Ile, Gly, Val, Leu, Nle, Phe, Gln or des $R_{41}$, provided however that when $R_{13}$ is His, then $R_{17}$ is Glu, $R_{18}$ is Val, $R_{22}$ is Thr, $R_{26}$ is Gln, $R_{28}$ is Ala, and $R_{36}$ is Lys; and provided that when $R_{13}$ is Glu, $R_{17}$ is Lys, $R_{18}$ is Met, $R_{22}$ is Glu, $R_{26}$ is Lys, $R_{28}$ is Lys, $R_{32}$ is Ala and $R_{36}$ is Leu, then either $R_1$ is not pGlu-Gly or $R_8$ is not Ile or $R_{11}$ is Thr or $R_{12}$ is not Leu or $R_{19}$ is not Ile or $R_{21}$ is not Ile or $R_{24}$ is not Gln or $R_{27}$ is not Glu or $R_{33}$ is not Asn or $R_{40}$ is not Thr or $R_{41}$ is not Ile.

The peptides are synthesized by a suitable method, such as by exclusively solid-phase techniques, by partial solid-phase techniques, by fragment condensation or by classical solution addition. CRF and certain analogs may also be synthesized by recently developed recombinant DNA techniques.

Common to chemical synthesis of peptides is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with various of these residues having side-chain protecting groups.

Also considered to be within the scope of the present invention are intermediates of the formula:

$X^1$-$R_1$-Pro-Pro-Ile-Ser($X^2$)-$R_8$-Asp($X^5$)-Leu
-$R_{11}$($X^2$)-$R_{12}$-$R_{13}$-Leu-Leu-Arg($X^3$)-$R_{17}$
-$R_{18}$-$R_{19}$-Glu($X^5$)-$R_{21}$-$R_{22}$-Lys($X^6$)-$R_{24}$-$R_{25}$($X^5$)-$R_2$
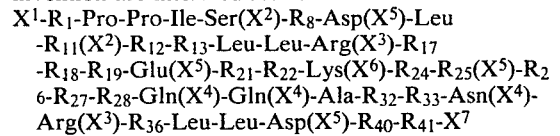
6-$R_{27}$-$R_{28}$-Gln($X^4$)-Gln($X^4$)-Ala-$R_{32}$-$R_{33}$-Asn($X^4$)-
Arg($X^3$)-$R_{36}$-Leu-Leu-Asp($X^5$)-$R_{40}$-$R_{41}$-$X^7$ wherein: the R-groups are as hereinbefore defined; $X^1$ is either hydrogen or an α-amino protecting group. The α-amino protecting groups contemplated by $X^1$ are those known to be useful in the art in the step-wise synthesis of polypeptides. Among the classes of α-amino protecting groups covered by $X^1$ are (1) acyl-type protecting groups, such as formyl, acrylyl(Acr), benzoyl(Bz) and acetyl(Ac) which are preferably used only at the N-terminal; (2) aromatic urethan-type protecting groups, such as benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethoxycarbonyl, isopropyloxycarbonyl, ethoxycarbonyl, allyloxycarbonyl; (4) cycloalkyl urethan-type protecting groups, such as cyclopentyloxycarbonyl, adamantyloxycarbonyl, and cyclohexyloxycarbonyl; and (5) thiourethan-type protecting groups, such as phenylthiocarbonyl. The preferred α-amino protecting group is BOC.

$X^2$ is a protecting group for the hydroxyl group of Thr and Ser and is preferably selected from the class consisting of acetyl(Ac), benzoyl(Bz), tert-butyl, triphenylmethyl(trityl), tetrahydropyranyl, benzyl ether(Bzl) and 2,6-dichlorobenzyl (DCB). The most preferred protecting group is Bzl. $X^2$ can be hydrogen, which means there is no protecting group on the hydroxyl group.

$X^3$ is a protecting group for the guanidino group of Arg preferably selected from the class consisting of nitro, p-toluenesulfonyl(Tos), Z, adamantyloxycarboyl and BOC, ir is hydrogen. Tos is most preferred.

$X^4$ is hydrogen or a protecting group for the amido group of Asn or Gln and is preferably xanthyl(Xan).

$X^5$ is hydrogen or an ester-forming protecting group for the β- or γ-carboxyl group of Asp or Glu, preferably selected from the class consisting of benzyl, 2,6-dichlorobenzyl, methyl, ethyl and t-butyl ester. OBzl is most preferred.

$X^6$ is hydrogen or a protecting group for the side chain amino substituent of Lys. Illustrative of suitable side chain amino protecting groups are Z, 2-chlorobenzyloxycarbonyl(2-Cl-Z), Tos, t-amyloxycarbonyl(Aoc), BOC and aromatic or aliphatic urethan-type protecting groups as specified hereinbefore.
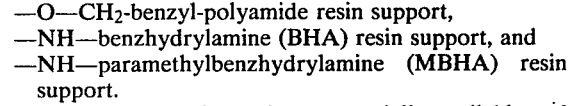
When Met is present, the sulfur may be protected, if desired, with oxygen. When His is present, the imidazole nitrogen can be protected with Tos or 2,4-dinitrophenyl(DNP). When Tyr is present, the hydroxyl group may be protected with DCB.

The selection of a side chain amino protecting group is not critical except that it must be one which is not removed during deprotection of the α-amino groups during the synthesis. Hence, the α-amino protecting group and the side chain amino protecting group cannot be the same.

$X^7$ is selected from the class consisting of OH, OCH$_3$, amides, hydrazides, esters and an amide anchoring bond used in solid phase synthesis for linking to a solid resin support, represented by the formulae:

—O—CH$_2$-benzyl-polyamide resin support,
—NH—benzhydrylamine (BHA) resin support, and
—NH—paramethylbenzhydrylamine (MBHA) resin support.

The polyamide polymer is commercially available and is discussed in detail in *Bioorganic Chemistry*, 8, 351–370 (1979) where a preferred version of it is discussed in FIG. 6. Use of BHA or MBHA resin is preferred, and cleavage gives the CRF amide or CRF analog amide.

In the formula for the intermediate, at least one of $X^1$, $X^2$, $X^3$, $X^4$, $X^5$ and $X^6$ is a protecting group. Depending upon the particular amino acids chosen for the R-groups, they may also have a protecting group attached as specified hereinbefore and as generally known in the art and mentioned hereinbefore. In selecting a particular side chain protecting group to be used in the synthesis of the peptides, the following rules are followed: (a) the protecting group must be stable to the reagent and under the reaction conditions selected for removing the α-amino protecting group at each step of the synthesis, (b) the protecting group must retain its protecting properties and not be split off under coupling conditions and (c) the side chain protecting group must be removable, upon the completion of the synthesis containing the desired amino acid sequence, under reaction conditions that will not alter the peptide chain.

For the acyl group represented by Z, acetyl, formyl, acrylyl and benzoyl are preferred. For the 1 to 10 amino acid peptide which may be optionally included without adversely affecting the potency, any amino acids may be used, but the L- or D- forms of the naturally accurring amino acids would normally be used.

The peptides are preferably prepared using solid phase synthesis, such as that described by Merrifield, *J.*

*Am. Chem. Soc.*, 85, p 2149 (1964), although other equivalent chemical syntheses known in the art can also be used as previously mentioned. Solid-phase synthesis is commenced from the C-terminal end of the peptide by coupling a protected α-amino acid to a suitable resin as generally set forth in U.S. Pat. No. 4,244,946 issued Jan. 21, 1981 to Rivier et al., the disclosure of which is incorporated herein by reference. Such a starting material for CRF can be prepared by attaching α-amino-protected Ala to a BHA resin.

Ala protected by BOC is coupled to the BHA resin using methylene chloride an dimethylformamide (DMF). Following the coupling of BOC-Ala to the resin support, the α-amino protecting group is removed, as by using trifluoroacetic acid(TFA) in methylene chloride, TFA alone or with HCl in dioxane. Preferably 50 weight % TFA in methylene chloride is used with 0–5 weight % 1,2-ethanedithiol. The deprotection is carried out at a temperature between about 0° C. and room temperature. Other standard cleaving reagents and conditions for removal of specific α-amino protecting groups may be used as described in Schroder & Lubke, "The Peptides", 1 pp 72–75 (Academic Press 1965).

After removal of the α-amino protecting group of Ala, the remaining α-amino- and side chain-protected amino acids are coupled step-wise in the desired order to obtain the intermediate compound defined hereinbefore. As an alternative to adding each amino acid separately in the synthesis, some of them may be coupled to one another prior to addition to the solid phase reactor. The selection of an appropriate coupling reagent is within the skill of the art. Particularly suitable as a coupling reagent is N,N'-dicyclohexyl carbodiimide (DCCI).

The activating reagents used in the solid phase synthesis of the peptides are well known in the peptide art. Examples of suitable activating reagents are carbodiimides, such as N,N'-diisopropyl carbodiimide and N-ethyl-N'-(3-dimethylaminopropyl)carbodiimide. Other activating reagents and their use in peptide coupling are described by Schroder & Lubke, supra, in Chapter III and by Kapoor, *J. Phar. Sci.*, 59, pp 1–27 (1970).

Each protected amino acid or amino acid sequence is introduced into the solid phase reactor in about a four-fold excess, and the coupling is carried out in a medium of dimethylformamide(DMF):$CH_2Cl_2$ (1:1) or in DMF or $CH_2Cl_2$ alone. In instances where the coupling is carried out manually, the success of the coupling reaction at each stage of the synthesis is monitored by the ninhydrin reaction, as described by E. Kaiser et al., *Anal. Biochem.* 34, 595 (1970). In cases where incomplete coupling occurs, the coupling procedure is repeated before removal of the α-amino protecting group prior to the coupling of the next amino acid. The coupling reactions can be performed automatically, as on a Beckman 990 automatic synthesizer, using a program such as that reported in Rivier et al., *Biopolymers*, 1978, 17, pp. 1927–1938.

After the desired amino acid sequence has been completed, the intermediate peptide is removed from the resin support by treatment with a reagent, such as liquid hydrogen fluoride, which not only cleaves the peptide from the resin but also cleaves all remaining side chain protecting groups $X^2$, $X^3$, $X^4$, $X^5$ and $X^6$ and the α-amino protecting group $X^1$ (unless it is an acyl group which is intended to be present in the final peptide), to obtain the peptide. When using hydrogen fluoride for cleaving, anisole and methylethyl sulfide are included in the reaction vessel as scavengers. When Met is present in the sequence, the BOC protecting group may be cleaved with trifluoroacetic acid(TFA)/ethanedithiol prior to cleaving the peptide from the resin to eliminate S-alkylation.

The following Example sets forth the preferred method for synthesizing analogs of CRF by the solid-phase technique.

EXAMPLE I

The synthesis of the CRF having the formula: H-Ser-Gln-Glu-Pro-Pro-Ile-Ser-Leu-Asp-Leu-Thr-Phe-His-Leu-Leu-Arg-Glu-Val-Leu-Glu-Met-Thr-Lys-Ala-Asp-Gln-Leu-Ala-Gln-Gln-Ala-His-Ser-Asn-Arg-Lys-Leu-Leu-Asp-Ile-Ala-$NH_2$ and a molecular weight of 4666 is conducted in a stepwise manner on a benzhydrylamine hydrochloride resin, such as available from Bachman, Inc., having a substitution range of about 0.1 to 0.5 mmoles/gm. resin. The synthesis is performed on an automatic Beckman 990A peptide synthesizer. Coupling of BOC-Ala results in the substitution of about 0.35 mmole. Ala per gram of resin. All solvents that are used are carefully degassed, preferably by sparging with an inert gas, e.g. helium or nitrogen, to insure the absence of oxygen that might undesirably oxidize the sulfur of the Met residue.

After deprotection and neutralization, the peptide chain is built step-by-step on the resin. Generally, one to two mmol. of BOC-protected amino acid in methylene chloride is used per gram of resin, plus one equivalent of 2 molar DCCI in methylene chloride, for two hours. When BOC—Arg(Tos) is being coupled, a mixture of 50% DMF and methylene chloride is used. Bzl is used as the hydroxyl side-chain protecting group for Ser and Thr. P-nitrophenyl ester(ONp) is used to activate the carboxyl end of Asn or Gln, and for example, BOC—Asn(ONp) is coupled overnight using one equivalent of HOBt in a 50% mixture of DMF and methylene chloride. The amido group of Asn or Gln is protected by Xan when DCC coupling is used instead of the active ester method. 2—Cl—Z is used as the protecting group for the Lys side chain. Tos is used to protect the guanidino group of Arg and the imidazole group of His, and the side chain carboxyl group of Glu or Asp is protected by OBzl. At the end of the synthesis, the following composition is obtained BOC-Ser(Bzl)-Gln(Xan)-Glu(OBzl)-Pro-Pro-Ile-Ser(Bzl)-Leu-Asp(OBzl)-Leu-Thr(Bzl)-Phe-His(Tos)-Leu-Leu-Arg(Tos)-Glu(OBzl)-Val-Leu-Glu(OBzl)-Met-Thr(Bzl)-Lys(2-Cl-Z)-Ala-Asp(OBzl)-Gln(Xan)-Leu-Ala-Gln(Xan)-Gln(Xan)-Ala-His(Tos)-Ser(Bzl)-Asn(Xan)-Arg(Tos)-Lys(2-Cl-Z)-Leu-Leu-Asp(OBzl)-Ile-Ala-resin support. Xan may have been partially or totally removed by TFA treatment used to deblock the α-amino protecting group.

In order to cleave and deprotect the resulting protected peptide-resin, it is treated with 1.5 ml. anisole, 0.5 ml. of methyl ethyl sulfide and 15 ml. hydrogen fluoride (HF) per gram of peptide-resin, first at −20° C. for 20 min. and then at 0.° C. for one-half hour. After elimination of the HF under high vacuum, the resin-peptide is washed alternately with dry diethyl ether and chloroform, and the peptides are then extracted with degassed 2 N aqueous acetic acid and separated from the resin by filtration.

The peptide is purified by gel permeation followed by semi-preparative HPLC as described in Rivier et al., Peptides: *Structure and Biological Function* (1979) pp. 125–128. The chromatographic fractions are carefully monitored by HPLC, and only the fractions showing substantial purity were pooled.

Specific optical rotation of the CRF peptide, which was synthesized and purified in the foregoing manner, was measured on a Perkin Elmer Model 141 as $[\alpha]_D^{22°} = -77.5° \pm 1.0$ (c=1 in 1% acetic acid) (without correcting for the presence of H₂O and TFA) and had a purity of about 96%. To check whether the precise sequence was achieved, the CRF peptide was hydroylzed in sealed evacuated tubes containing 4 N methanesulfonic acid and 0.2% tryptamine for 24 hours at 110° C. Amino acid analyses of the hydrolysates using a Beckman 121 MB amino acid analyzer showed the following amino acid ratios: Asp(4.02), Thr(1.85), Ser(2.76), Glu(7.0), Pro(1.58), Ala(4.03), Val(0.96), Met(0.95), Ile(1.93), Leu(8.15), Phe(1.00), Lys(2.00), His(1.95) and Arg(1.98), which confirmed that the 41-residue peptide structure had been obtained.

EXAMPLE II

CRF was extracted, isolated and purified in the following manner. 490,000 ovine hypothalamic fragments were extracted in ethanol-acetic acid-chloroform, defatted with a mixture of ethyl ether and petroleum ether and subjected to repeated shake-out with the partition system 0.1% acetic acid:n-butanol:pyridine (11:5:3). The combined aqueous phases show ACTH-releasing activity.

Following dialysis (Spectrapor 3) against 2 N HOAc, about 350,000 fragment equivalents of the retentates weighing 15 grams were subjected to gel filtration on Sephadex G-50. The bulk of material was chromatographed at cold room temperatures in 9 successive runs using a 3.1×150 cm. G-50 column eluted with 2 N HOAc. The zone showing the most significant ACTH-releasing activity eluted at about 1.3 $V_e/V_o$.

A portion of the material from this zone, about 130,000 fragment equivalents, was subjected to ion exchange on SP-Sephadex. The sample was applied in 0.01 M ammonium formate buffer, pH 3.2 and eluted with a linear gradient of the application buffer to 1:5 M ammonium formate, pH 7.0. ACTH releasing activity was weakly absorbed. The ACTH releasing fraction from SP-Sephadex and the remainder of the zone from Sephadex-G-50 were dissolved in 6 M guanidine HCl/HOAc, pH 2.5, heated 5 min. at 90°, then chromatographed on Biogel P-10 with 4 M guanidine HCl/HOAc, ph 2.5. The ACTH-releasing fractions were pooled and purified further by successive high pressure liquid chromatographic (HPLC) steps which included: (1) Reverse phase HPLC on μBondapak CN (Waters and Associates) using a gradient of decreasing triethylammonium phosphate (TEAP) and increasing acetonitrile; (2) Reverse phase HPLC on μBondapak C₁₈ (Waters and Associates) with TEAP/acetonitrile; and either 3a) Reverse phase HPLC on μBondapak CN with gradients of triethylammonium formate and acetronitrile, or 3b) Reverse phase HPLC on C₁₈ with gradients of trifluoroacetic acid and acetonitrile. Lyophilized active zones from both HPCL steps 3a or 3b were used for composition and structural analysis which gave the following sequence:

H-Ser-Gln-Glu-Pro-Pro-Ile-Ser-Leu-Asp-Leu-Thr-
    Phe-His-Leu-Leu-Arg-Glu-Val-Leu-Glu-Met-Thr-
    Lys-Ala-Asp-Gln-Leu-Ala-Gln-Gln-Ala-His-Ser-
    Asn-Arg-Lys-Leu-Leu-Asp-Ile-Ala-NH₂.

EXAMPLE III

The synthetic and the natural CRF were examined for their effects on the secretion of ACTH and β-endorphin in vitro and the synthetic CRF was also examined in vivo. The high potency of synthetic and natural CRF to stimulate the secretion of ACTH and β-endorphin by cultured rat pituitary cells was measured. Minimal and half-maximal responses were observed at about 10 picomolar and about 100 picomolar of synthetic CRF, respectively. The secretory response to maximal (>5 nM) concentrations of CRF is at a plateau level. In vivo doses from 30 ng to 3 μg/Kg of body weight rapidly elevated ACTH and β-endorphin-like (β-END-LI) secretions 5–20 fold.

Synthetic CRF has been shown to be a powerful stimulator of ACTH and β-END-LI secretion in vivo in several rat preparations. Plasma levels of ACTH and β-END-LI are elevated for at least 5–20 minutes following the intravenous administration of CRF to nembutal-anesthesized male rats and to quiescent male or female rats with indwelling intravenous cannulae. In addition, CRF is found to have a dramatic effect upon blood pressure in rats and dogs. Mean cartoid blood pressure in a urethane-anesthesized rat fell from 87 to 72±2 mm Hg and remained at that level for 30 minutes following an injection equal to 3 μg CRF/Kg body weight; the subsequent administration of an injection equal to 30 μg CRF/Kg body weight lowered mean blood pressure to 42±3 mm Hg for more than 2 hours.

EXAMPLE IV

The peptide [des Ser¹-Gln²-Glu³]-CRF having the formula:
H-Pro-Pro-Ile-Ser-Leu-Asp-Leu-Thr-Phe-His-Leu-
    Leu-Arg-Glu-Val-Leu-Glu-Met-Thr-Lys-Ala-Asp-
    Gln-Leu-Ala-Gln-Gln-Ala-His-Ser-Asn-Arg-Lys-
    Leu-Leu-Asp-Ile-Ala-NH₂ is synthesized. Testing in accordance with the general procedure set forth in Example III shows that it likewise stimulates the secretion of ACTH and β-END-LI and causes a very significant lowering of blood pressure.

EXAMPLE V

The peptide [des pGlu¹-Gly²]-sauvagine having the formula:
H-Pro-Pro-Ile-Ser-Ile-Asp-Leu-Ser-Leu-Glu-Leu-Leu-
    Arg-Lys-Met-Ile-Glu-Ile-Glu-Lys-Gln-Glu-Lys-
    Glu-Lys-Gln-Gln-Ala-Ala-Asn-Asn-Arg-Leu-Leu-
    Leu-Asp-Thr-Ile-NH₂ is synthesized. Testing in accordance with the general procedure set forth in Example III shows that it likewise stimulates the secretion of ACTH and β-END-LI and causes a very significant lowering of blood pressure.

EXAMPLE VI

The peptide [des Ala⁴¹]-CRF having the formula:
H-Ser-Gln-Glu-Pro-Pro-Ile-Ser-Leu-Asp-Leu-Thr-
    Phe-His-Leu-Leu-Arg-Glu-Val-Leu-Glu-Met-Thr-
    Lys-Ala-Asp-Gln-Leu-Ala-Gln-Gln-Ala-His-Ser-
    Asn-Arg-Lys-Leu-Leu-Asp-Ile-NH₂ is synthesized. Testing in accordance with the general procedure set forth in Example III shows that it likewise stimulates the secretion of ACTH and β-END-LI and causes a very significant lowering of blood pressure.

EXAMPLE VII

The peptide [Acetyl-Ala$^1$]-CRF having the formula:
Ac-Ala-Gln-Glu-Pro-Pro-Ile-Ser-Leu-Asp-Leu-Thr-
Phe-His-Leu-Leu-Arg-Glu-Val-Leu-Glu-Met-Thr-
Lys-Ala-Asp-Gln-Leu-Ala-Gln-Gln-Ala-His-Ser-
Asn-Arg-Lys-Leu-Leu-Asp-Ile-Ala-NH$_2$
is synthesized. Testing in accordance with the general procedure set forth in Example III shows that it likewise stimulates the secretion of ACTH and β-END-LI and causes a very significant lowering of blood pressure.

EXAMPLE VIII

The peptide [Ile$^{19}$, Glu$^{25}$]-CRF having the formula:
H-Ser-Gln-Glu-Pro-Pro-Ile-Ser-Leu-Asp-Leu-Thr-
Phe-His-Leu-Leu-Arg-Glu-Val-Ile-Glu-Met-Thr-
Lys-Ala-Glu-Gln-Leu-Ala-Gln-Gln-Ala-His-Ser-
Asn-Arg-Lys-Leu-Leu-Asp-Ile-Ala-NH$_2$
is synthesized. Testing in accordance with the general procedure set forth in Example III shows that it likewise stimulates the secretion of ACTH and β-END-LI and causes a very significant lowering of blood pressure.

EXAMPLE IX

The peptide [Tyr$^{13}$, Nle$^{21}$]-CRF having the formula:
H-Ser-Gln-Glu-Pro-Pro-Ile-Ser-Leu-Asp-Leu-Thr-
Phe-Tyr-Leu-Leu-Arg-Glu-Val-Leu-Glu-Nle-Thr-
Lys-Ala-Asp-Gln-Leu-Ala-Gln-Gln-Ala-His-Ser-
Asn-Arg-Lys-Leu-Leu-Asp-Ile-Ala-NH$_2$
is synthesized. Testing in accordance with the general procedure set forth in Example III shows that it likewise stimulates the secretion of ACTH and β-END-LI and causes a very significant lowering of blood pressure to a greater extent than CRF.

EXAMPLE X

The peptide [Ile$^8$, Ser$^{11}$, Asn$^{33}$]-CRF having the formula:
H-Ser-Gln-Glu-Pro-Pro-Ile-Ser-Ile-Asp-Leu-Ser-Phe-
His-Leu-Leu-Arg-Glu-Val-Leu-Glu-Met-Thr-Lys-
Ala-Asp-Gln-Leu-Ala-Gln-Gln-Ala-His-Asn-Asn-
Arg-Lys-Leu-Leu-Asp-Ile-Ala-NH$_2$
is synthesized. Testing in accordance with the general procedure set forth in Example III shows that it likewise stimulates the secretion of ACTH and β-END-LI and causes a very significant lowering of blood pressure.

EXAMPLE XI

The peptide [Acrylyl-Phe-Gly-Ala$^1$, Ser$^2$]-CRF having the formula:
Acr-Phe-Gly-Ala-Ser-Glu-Pro-Pro-Ile-Ser-Leu-Asp-
Leu-Thr-Phe-His-Leu-Leu-Arg-Glu-Val-Leu-Glu-
Met-Thr-Lys-Ala-Asp-Gln-Leu-Ala-Gln-Gln-Ala-
His-Ser-Asn-Arg-Lys-Leu-Leu-Asp-Ile-Ala-NH$_2$
is synthesized. Testing in accordance with the general procedure set forth in Example III shows that it likewise stimulates the secretion of ACTH and β-END-LI and causes a very significant lowering of blood pressure.

EXAMPLE XII

The peptide [Benzoyl-Ala$^1$, des Gln$^2$, Leu$^{12}$]-CRF having the formula:
Bz-Ala-Glu-Pro-Pro-Ile-Ser-Leu-Asp-Leu-Thr-Leu-
His-Leu-Leu-Arg-Glu-Val-Leu-Glu-Met-Thr-Lys-
Ala-Asp-Gln-Leu-Ala-Gln-Gln-Ala-His-Ser-Asn-
Arg-Lys-Leu-Leu-Asp-Ile-Ala-NH$_2$
is synthesized. Testing in accordance with the general procedure set forth in Example III shows that it likewise stimulates the secretion of ACTH and β-END-LI and causes a very significant lowering of blood pressure.

EXAMPLE XIII

The peptide [Ala$^{21}$, Thr$^{33}$, Nle$^{41}$]-CRF having the formula:
H-Ser-Gln-Glu-Pro-Pro-Ile-Ser-Leu-Asp-Leu-Thr-
Phe-His-Leu-Leu-Arg-Glu-Val-Leu-Glu-Ala-Thr-
Lys-Ala-Asp-Gln-Leu-Ala-Gln-Gln-Ala-His-Thr-
Asn-Arg-Lys-Leu-Leu-Asp-Ile-Nle-NH$_2$
is synthesized. Testing in accordance with the general procedure set forth in Example III shows that it likewise stimulates the secretion of ACTH and β-END-LI and causes a very significant lowering of blood pressure.

EXAMPLE XIV

The peptide [Ala$^{39}$, Ala$^{40}$]-sauvagine having the formula:
pGlu-Gly-Pro-Pro-Ile-Ser-Ile-Asp-Leu-Ser-Leu-Glu-
Leu-Leu-Arg-Lys-Met-Ile-Glu-Ile-Glu-Lys-Gln-
Glu-Lys-Glu-Lys-Gln-Gln-Ala-Ala-Asn-Asn-Arg-
Leu-Leu-Leu-Asp-Ala-Ala-NH$_2$
is synthesized. Testing in accordance with the general procedure set forth in Example III shows that it likewise stimulates the secretion of ACTH and β-END-LI and causes a very significant lowering of blood pressure.

EXAMPLE XV

The peptide [Gly$^{26}$]-sauvagine having the formula:
pGlu-Gly-Pro-Pro-Ile-Ser-Ile-Asp-Leu-Ser-Leu-Glu-
Leu-Leu-Arg-Lys-Met-Ile-Glu-Ile-Glu-Lys-Gln-
Glu-Lys-Gly-Lys-Gln-Gln-Ala-Ala-Asn-Asn-Arg-
Leu-Leu-Leu-Asp-Thr-Ile-NH$_2$
is synthesized. Testing in accordance with the general procedure set forth in Example III shows that it likewise stimulates the secretion of ACTH and β-END-LI and causes a very significant lowering of blood pressure.

EXAMPLE XVI

The peptide [Acetyl-Pro$^4$]-CRF having the formula:
Ac-Pro-Pro-Ile-Ser-Leu-Asp-Leu-Thr-Phe-His-Leu-
Leu-Arg-Glu-Val-Leu-Glu-Met-Thr-Lys-Ala-Asp-
Gln-Leu-Ala-Gln-Gln-Ala-His-Ser-Asn-Arg-Lys-
Leu-Leu-Asp-Ile-Ala-NH$_2$
is synthesized. Testing in accordance with the general procedure set forth in Example III shows that it likewise stimulates the secretion of ACTH and β-END-LI and causes a very significant lowering of blood pressure to a greater extent than CRF.

EXAMPLE XVII

The peptide [Nle$^{21}$, Tyr$^{32}$]-CRF having the formula:

H-Ser-Gln-Glu-Pro-Pro-Ile-Ser-Leu-Asp-Leu-Thr-
Phe-His-Leu-Leu-Arg-Glu-Val-Leu-Glu-Nle-Thr-
Lys-Ala-Asp-Gln-Leu-Ala-Gln-Gln-Ala-Tyr-Ser-
Asn-Arg-Lys-Leu-Leu-Asp-Ile-Ala-NH$_2$ is synthesized. Testing in accordance with the general procedure set forth in Example III shows that it likewise stimulates the secretion of ACTH and β-END-LI and causes a very significant lowering of blood pressure to a greater extent than CRF.

EXAMPLE XVIII

The peptide [Met(O)$^{21}$]-CRF having the formula:
H-Ser-Gln-Glu-Pro-Pro-Ile-Ser-Leu-Asp-Leu-Thr-
Phe-His-Leu-Leu-Arg-Glu-Val-Leu-Glu-Met(O)-
Thr-Lys-Ala-Asp-Gln-Leu-Ala-Gln-Gln-Ala-His-
Ser-Asn-Arg-Lys-Leu-Leu-Asp-Ile-Ala-NH$_2$ is synthesized. Testing in accordance with the general procedure set forth in Example III shows that it likewise stimulates the secretion of ACTH and β-END-LI and causes a very significant lowering of blood pressure.

It is of interest that CRF and its analogs exhibited such an extreme lowering of blood pressure. As a result, these peptides may be particularly valuable for the treatment of high blood pressure conditions and also for the treatment of patients who are to undergo certain types of surgery.

As CRF profoundly stimulates the pituitary-adrenalcortical axis, CRF or its analogs should be useful to stimulate the functions of this axis in some types of patients with low endogenous glucocorticoid production. For example, CRF should be useful in restoring pituitary-adrenal function in patients having received exogenous glucocorticoid therapy whose adrenalcortical functions remain supressed.

Most other regulatory peptides have been found to have effects upon the central nervous system and upon the gastrointestinal tract. Because ACTH and β-END secretion is the "sine qua non" of an animal's response to stress, it is likely that CRF should have significant effects on the brain as a mediator or limiter of the body's stress response. Accordingly, CRF may also find application in modifying the mood and behavior of normal and mentally disordered individuals. Because CRF and its analogs elevate the levels of ACTH, β-END, β-lipotropin and corticosterone, its administration can be used to induce their effects on the brain and its periphery to thereby influence memory, mood, pain appreciation, etc., and more specifically, alertness, depression and/or anxiety.

It is also believed that relatively larger amounts of CRF or some of its more potent analogs may function in a manner similar to the way that GnRH superagonists inhibit reproductive functions. Thus, these peptides may be able to desensitize CRF target organs and thus be valuable in the treatment of subjects with Cushing's disease and similar disorders.

CRF, its analogs or the nontoxic addition salts thereof, combined with a pharmaceutically acceptable carrier to form a pharmaceutical composition, may be administered to mammals, including humans, either intravenously, subcutaneously, intramuscularly, intranasally, intracerebrospinally or orally. The peptides should be at least about 93% pure and preferably should have a purity of at least about 98%. This purity means that the intended peptide constitutes the stated weight % of all like peptides and peptide fragments present. Their administration may be employed by a physician to lower blood pressure or to stimulate endogenous gluco-corticoid production. The required dosage will vary with the particular condition being treated, with the severity of the condition and with the duration of desired treatment.

Such peptides are often administered in the form of pharmaceutically acceptable nontoxic salts, such as acid addition salts or metal complexes, e.g., with zinc, iron, calcium, barium, magnesium, aluminum or the like (which are considered as addition salts for purposes of this application). Illustrative of such acid addition salts are hydrochloride, hydrobromide, sulphate, phosphate, tannate, pamoate, oxalate, fumarate, gluconate, alginate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptides should be administered under the guidance of a physician, and pharmaceutical compositions will usually contain the peptide in conjunction with a conventional, pharmaceutically-acceptable carrier. Usually, the dosage will be from about 1 to about 200 micrograms of the peptide per kilogram of the body weight of the host. In some instances, treatment of subjects with these peptides can be carried out in lieu of the administration of ACTH or corticosteroids, in such instances a dosage as low as about 10 ng/Kg of body weight may be employed. As used herein all temperatures are °C. and all ratios are by volume. Percentages of liquid materials are also by volume.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, substitutions and modifications at other positions in the CRF peptide chain can be made in accordance with present or future developments without detracting from the potency of the analogs, and such peptides are considered as being within the scope of the invention.

Various features of the invention are emphasized in the claims which follow.

What is claimed is:

1. A pharmaceutical composition for lowering the blood pressure of a mammal and/or for elevating the secretion of ACTH and corticosteroids comprising CRF or analogs of CRF or the nontoxic addition salts thereof having the formula:
Z-R$_1$-Pro-Pro-Ile-Ser-R$_8$-Asp-Leu-R$_{11}$-R$_{12}$-
R$_{13}$-Leu-Leu-Arg-R$_{17}$-R$_{18}$-R$_{19}$-Glu-R$_{21}$-
R$_{22}$-Lys-R$_{24}$-R$_{25}$-R$_{26}$-R$_{27}$-R$_{28}$-Gln-Gln-Ala-R$_{32}$-R$_{33}$-
Asn-Arg-R$_{36}$-Leu-Leu-Asp-R$_{40}$-R$_{41}$-NH$_2$
wherein Z is an acyl group having 7 or less carbon atoms or hydrogen; R$_1$ is Ser-Gln-Glu or pGlu-Gly or Gln-Glu or Glu or D-Ser-Gln-Glu or D-pGlu-Gly or desR$_1$; R$_8$, R$_{12}$, R$_{19}$, R$_{24}$ and R$_{40}$ are selected from the group consisting of Leu, Ile, Ala, Gly, Val, Nle, Phe and Gln; R$_{11}$ is Thr or Ser; R$_{13}$ is His, Tyr or Glu; R$_{17}$ is Glu or Lys; $R_{18}$ is Val or Met; $R_{21}$ is Met, Met(O), Ile, Ala, Leu, Gly, Nle, Val, Phe or Gln; $R_{22}$ is Thr or Glu; $R_{25}$ is Asp or Glu; $R_{26}$ is Gln or Lys; $R_{27}$ is Leu, Ile, Ala, Gly, Val, Nle, Phe, Asp, Asn, Gln or Glu; $R_{28}$ is Ala or Lys; $R_{32}$ is His, Tyr or Ala; $R_{33}$ is Ser, Asn, Thr or Ala; $R_{36}$ is Lys or Leu; $R_{41}$ is Ala, Ile, Gly, Val, Leu, Nle, Phe, Gln or des $R_{41}$, provided however that when $R_{13}$ is His, then $R_{17}$ is Glu, $R_{18}$ is Val, $R_{22}$ is Thr, $R_{26}$ is Gln, $R_{28}$ is Ala, and $R_{36}$ is Lys; and provided that when $R_{13}$ is Glu, $R_{17}$ is Lys, $R_{18}$ is Met, $R_{22}$ is Glu, $R_{26}$ is Lys, $R_{28}$ is Lys, $R_{32}$ is Ala and $R_{36}$ is Leu, then either $R_1$ is not pGlu-Gly or $R_8$ is not Ile or $R_{11}$ is Thr or $R_{12}$ is not Leu or $R_{19}$ is not Ile or $R_{21}$ is not Ile or $R_{24}$ is not Gln or $R_{27}$ is not Glu or $R_{33}$ is not Asn or $R_{40}$ is not Thr or $R_{41}$ is not Ile, and a pharmaceutically acceptable liquid or solid carrier therefor.

2. A method for lowering the blood pressure of a mammal, which method comprises administering to said mammal an effective amount of a material selected from the class consisting of CRF, analogs of CRF, and the nontoxic addition salts thereof, having the formula:
Z-$R_1$-Pro-Pro-Ile-Ser-$R_8$-Asp-Leu-$R_{11}$-$R_{12}$-$R_{13}$-Leu-Leu-Arg-$R_{17}$-$R_{18}$-$R_{19}$-Glu-$R_{21}$-$R_{22}$-Lys-$R_{24}$-$R_{25}$-$R_{26}$-$R_{27}$-$R_{28}$ -Gln-Gln-Ala-$R_{32}$-$R_{33}$-Asn-Arg-$R_{36}$-Leu-Leu-Asp-$R_{40}$-$R_{41}$-NH$_2$
wherein Z is an acyl group having 7 or less carbon atoms or hydrogen; $R_1$ is Ser-Gln-Glu or pGlu-Gly or Gln-Glu or Glu or D-Ser-Gln-Glu or D-pGlu-Gly or des$R_1$; $R_8$, $R_{12}$, $R_{19}$, $R_{24}$ and $R_{40}$ are selected from the group consisting of Leu, Ile, Ala, Gly, Val, Nle, Phe and Gln; $R_{11}$ is Thr or Ser; $R_{13}$ is His, Tyr or Glu; $R_{17}$ is Glu or Lys; $R_{18}$ is Val or Met; $R_{21}$ is Met, Met(O), Ile, Ala, Leu, Gly, Nle, Val, Phe or Gln; $R_{22}$ is Thr or Glu; $R_{25}$ is Asp or Glu; $R_{26}$ is Gln or Lys; $R_{27}$ is Leu, Ile, Ala, Gly, Val, Nle, Phe, Asp, Asn, Gln or Glu; $R_{28}$ is Ala or Lys; $R_{32}$ is His, Tyr or Ala; $R_{33}$ is Ser, Asn, Thr, or Ala; $R_{36}$ is Lys or Leu; $R_{41}$ is Ala, Ile, Gly, Val, Leu, Nle, Phe, Gln or des $R_{41}$, provided however that when $R_{13}$ is His, then $R_{17}$ is Glu, $R_{18}$ is Val, $R_{22}$ is Thr, $R_{26}$ is Gln, $R_{28}$ is Ala, and $R_{36}$ is Lys; and provided that when $R_{13}$ is Glu, $R_{17}$ is Lys, $R_{18}$ is Met, $R_{22}$ is Glu, $R_{26}$ is Lys, $R_{28}$ is Lys, $R_{32}$ is Ala and $R_{36}$ is Leu, then either $R_1$ is not pGlu-Gly or $R_8$ is not Ile or $R_{11}$ is Thr or $R_{12}$ is not Leu or $R_{19}$ is not Ile or $R_{21}$ is not Ile or $R_{24}$ is not Gln or $R_{27}$ is not Glu or $R_{33}$ is not Asn or $R_{40}$ is not Thr or $R_{41}$ is not Ile.

3. A method in accordance with claim 2 wherein said administering is carried out either orally, intravenously, subcutaneously, intranasally, intracerebrospinally or intramuscularly.

4. Z-$R_1$-Pro-Pro-Ile-Ser-$R_8$-Asp-Leu-$R_{11}$-$R_{12}$-$R_{13}$-Leu-Leu-Arg-$R_{17}$-$R_{18}$-$R_{19}$-Glu-$R_{21}$-$R_{22}$-Lys-$R_{24}$-$R_{25}$-$R_{26}$-$R_{27}$-$R_{28}$-Gln-Gln-Ala-$R_{32}$-$R_{33}$-Asn-Arg-$R_{36}$-Leu-Leu-Asp-$R_{40}$-$R_{41}$-NH$_2$ wherein Z is an acyl group having 7 or less carbon atoms or hydrogen; $R_1$ is Ser-Gln-Glu or pGlu-GLy or Gln-Glu or GLu or D-Ser-Gln-Glu or D-pGlu-Gly or des$R_1$; $R_8$, $R_{12}$, $R_{19}$, $R_{24}$ and $R_{40}$ are selected from the group consisting of Leu, Ile, Ala, Gly, Val, Nle, Phe and Gln; $R_{11}$ is Thr or Ser; $R_{13}$ is His, Tyr or Glu; $R_{17}$ is Glu or Lys; $R_{18}$ is Val or Met; $R_{21}$ is Met, Met(O), Ile, Ala, Leu, Gly, Nle, Val, Phe or Gln; $R_{22}$ is Thr or Glu; $R_{25}$ is Asp or Glu; $R_{26}$ is Gln or Lys; $R_{27}$ is Leu, Ile, Ala, Gly, Val, Nle, Phe, Asp, Asn, Gln or Glu; $R_{28}$ is Ala or Lys; $R_{32}$ is His, Tyr or Ala; $R_{33}$ is Ser, Asn, Thr or Ala; $R_{36}$ is Lys or Leu; $R_{41}$ is Ala, Ile, Gly, Val, Leu, Nle, Phe, Gln or des $R_{41}$, provided however that when $R_{13}$ is His, then $R_{17}$ is Glu, $R_{18}$ is Val, $R_{22}$ is Thr, $R_{26}$ is Gln, $R_{28}$ is Ala, and $R_{36}$ is Lys; and provided that when $R_{13}$ is Glu, $R_{17}$ is Lys, $R_{18}$ is Met, $R_{22}$ is Glu, $R_{26}$ is Lys, $R_{28}$ is Lys, $R_{32}$ is Ala and $R_{36}$ is Leu, then either $R_1$ is not pGlu-Gly or $R_8$ is not Ile or $R_{11}$ is Thr or $R_{12}$ is not Leu or $R_{19}$ is not Ile or $R_{21}$ is not Ile or $R_{24}$ is not Gln or $R_{27}$ is not Glu or $R_{33}$ is not Asn or $R_{40}$ is not Thr or $R_{41}$ is not Ile; or a nontoxic addition salt thereof.

5. The compound of claim 4 wherein $R_{13}$ is His.

6. The compound of claim 5 wherein $R_{21}$ is Met.

7. The compound of claim 4 wherein $R_{13}$ is Tyr.

8. The compound of claim 4 wherein $R_{32}$ is Tyr.

9. The compound of either claim 7 or 8 wherein $R_{21}$ is Nle.

10. The compound of claim 5 wherein $R_{25}$ is Glu.

11. The compound of claim 5 wherein $R_{25}$ is Asp.

12. The compound of claim 11 wherein $R_{33}$ is Ser.

13. The compound of claim 12 wherein $R_{41}$ is Ala.

14. The compound of claim 13 wherein $R_{11}$ is Thr.

15. The compound of claim 11 wherein $R_8$ is Leu, $R_{12}$ is Phe, $R_{19}$ is Leu, $R_{24}$ is Ala, $R_{27}$ is Leu and $R_{40}$ is Ile.

16. The compound of claim 4 wherein $R_1$ is Ser-Gln-Glu and Z is H.

17. The compound of claim 4 wherein Z is Ac and $R_1$ is des $R_1$.

18. The compound of claim 4 wherein $R_{41}$ is des $R_{41}$.

19. The compound of claim 4 wherein $R_{41}$ is Nle.

20. The compound of claim 4 having the formula:
H-Ser-Gln-Glu-Pro-Pro-Ile-Ser-Leu-Asp-Leu-Thr-Phe-His-Leu-Leu-Arg-Glu-Val-Leu-Glu-Met-Thr-Lys-Ala-Asp-Gln-Leu-Ala-Gln-Gln-Ala-His-Ser-Asn-Arg-Lys-Leu-Leu-Asp-Ile-Ala-NH$_2$
and being at least about 93% pure.

21. The compound of claim 4 having the formula:
H-Pro-Pro-Ile-Ser-Ile-Asp-Leu-Ser-Leu-Glu-Leu-Leu-Arg-Lys-Met-Ile-Glu-Ile-Glu-Lys-Gln-Glu-Lys-Gly-Lys-Gln-Gln-Ala-Ala-Asn-Asn-Arg-Leu-Leu-Leu-Asp-Thr-Ile-NH$_2$.

22. The compound of claim 4 wherein $R_{11}$ is Glu, $R_{18}$ is Val, $R_{22}$ is Thr, $R_{25}$ is Asp, $R_{26}$ is Gln, $R_{28}$ is Ala and $R_{36}$ is Lys.

23. The compound of claim 22 wherein $R_8$ is Leu, $R_{11}$ is Thr, $R_{12}$ is Phe, $R_{19}$ is Leu, $R_{24}$ is Ala, $R_{27}$ is Leu, $R_{33}$ is Ser and $R_{40}$ is Ile.

24. The compound of claim 23 wherein $R_{32}$ is Tyr.

25. The compound of claim 24 wherein $R_{21}$ is Nle.

26. The compound of claim 24 or 25 wherein $R_{13}$ is Tyr.

27. The compound of claim 22 wherein $R_{13}$ is Tyr and $R_{21}$ is Nle.

28. The compound of either claim 25 or 27 wherein $R_1$ is Ser-Gln-Glu and $R_{41}$ is Ala.

29. The compound of claim 4 wherein $R_{21}$ is Met(O).

30. A method of elevating the secretion of ACTH and corticosteroids which comprises administering an effective amount of the compound of claim 4.

31. A method of elevating the secretion of β-END-LI, which comprises administering an effective amount of the compound of claim 4.

* * * * *

UNITED STATES PATENT AND TRADEMARK OFFICE
CERTIFICATE OF CORRECTION

PATENT NO. : 4,415,558

DATED : November 15, 1983

INVENTOR(S) : Vale, Spiess, C. Rivier and J. Rivier

It is certified that error appears in the above-identified patent and that said Letters Patent is hereby corrected as shown below:

Col. 4, line 6, correct the spelling of "or"

Col. 14, line 43, "$R_{11}$" should read --$R_{17}$--.

Signed and Sealed this

Second Day of April 1985

[SEAL]

Attest:

DONALD J. QUIGG

Attesting Officer     Acting Commissioner of Patents and Trademarks